United States Patent [19]
Pickart

[11] Patent Number: 5,164,367
[45] Date of Patent: Nov. 17, 1992

[54] METHOD OF USING COPPER(II) CONTAINING COMPOUNDS TO ACCELERATE WOUND HEALING

[75] Inventor: Loren R. Pickart, Bellevue, Wash.

[73] Assignee: ProCyte Corporation, Redmond, Wash.

[21] Appl. No.: 499,606

[22] Filed: Mar. 26, 1990

[51] Int. Cl.⁵ .............................................. A61K 37/14
[52] U.S. Cl. .......................................... 514/6; 514/15; 514/16; 514/17; 514/18; 514/19; 530/328; 530/329; 530/330; 530/331
[58] Field of Search .................. 514/18, 19, 6, 15–17; 530/330, 331, 328, 329

[56] References Cited

U.S. PATENT DOCUMENTS

| | | | |
|---|---|---|---|
| 3,194,732 | 7/1965 | Neuhauser | 167/58 |
| 3,551,554 | 12/1970 | Herschler | 424/7 |
| 3,558,770 | 1/1971 | Gordon et al. | 424/80 |
| 3,758,682 | 9/1973 | Huber et al. | 424/177 |
| 3,767,784 | 10/1973 | Gluck | 424/28 |
| 3,832,338 | 8/1974 | Huber et al. | 260/113 |
| 4,022,888 | 5/1977 | Huber et al. | 424/177 |
| 4,167,945 | 9/1979 | Gottlieb | 128/334 R |
| 4,177,261 | 12/1979 | Dietze et al. | 424/101 |
| 4,263,428 | 4/1981 | Apple et al. | 536/17 A |
| 4,287,184 | 9/1981 | Young | 424/177 |
| 4,440,788 | 4/1984 | Terayama et al. | 424/320 |
| 4,665,054 | 5/1987 | Pickart | 514/18 |
| 4,760,051 | 7/1988 | Pickart | 514/6 |
| 4,767,753 | 8/1988 | Pickart | 514/18 |
| 4,810,693 | 3/1989 | Pickart | 514/18 |

FOREIGN PATENT DOCUMENTS

| | | |
|---|---|---|
| 0078228 | 4/1982 | European Pat. Off. |
| 86/00222 | 1/1986 | PCT Int'l Appl. |
| 88/08695 | 11/1988 | PCT Int'l Appl. |
| 88/08715 | 11/1988 | PCT Int'l Appl. |

OTHER PUBLICATIONS

Pickart et al., "Growth-Modulating Tripeptide (glycylhistidyllysine): Association with Copper and Iron in Plasma and Stimulation of Adhesive and Growth of Hepatoma Cells in Culture by Tripeptide-Metal Ion Complexes," *J. Physiol.* 102(2):129–139, 1980.
Williams et al., "Glycyl-L-Histidyl-L-Lysine, a Growth Promoting Factor for Human Cells," *Cytobios* 27(105):19–25, 1980.
Mochida Pharmaceutical Co. Ltd., "Anti-Inflammatory Injections Containing Superoxide Dismutase," Jpn. Kokai Tokkyo Koho, 81 07,720,27 Jan. 1981 (cited in *Chem. Abstracts* 94:145386f, 1981).
Kwa, "Glycyl-L-Histidyl-L-Lysine: Synthesis of Analogs and NMR Studies," Ph.D. Thesis, University of Washington, 1983.
Loker, "Synthesis of Blood Serum Peptide Cell Growth Factors," Ph.D. Thesis, University of Washington, 1980.
Pickart, "The Biological Effects and Mechanism of Action of the Plasma Tripeptide Glycyl-L-Histidyl-L-Lysine," *Lymphonkines* 8:425–446, 1983.
Poole et al., "Stimulation of Rat Peritoneal Mast Cell Migration by Tumor-Derived Peptides," *Cancer Research* 43:5857–5861, 1983.
Raju et al., "Ceruloplasmin, Copper Ions, and Angiogenesis," *JNCI* 69(5):1183–1188, 1982.
Freedman et al., "Structure of the Glycyl-L-Histidyl-L-Lysine-Copper(II) Complex in Solution," *Biochemistry* 21:4540–4544, 1982.
Kwa et al., "PMR Studies of Cu(II) and Zn(II) Interaction with Glycyl-L-Histidyl-L-Lysine and Related Peptides," *Peptides: Structure and Function* 8:805–808, 1983.
Perkins et al., "The Structure of a Copper Complex of the Growth Factor Glycyl-L-Histidyl-L-Lysine at 1.1 A Resolution," *Inorganica Chimica Acta* 82:93–99, 1984.
Kimoto et al., "Enhancement of Antitumor Activity of Ascorbate Against Ehrlich Ascites Tumor Cells by the Copper: Glycylglycylhistidine Complex," *Cancer Research* 43824–828, 1983.
Sorenson, "Copper Complexes: A Physiologic Approach to Treatment of Chronic Diseases," *Comprehensive Therapy* 11(4):49–64, 1985.
Pickart et al., "Inhibition of the Growth of Cultured Cells and an Implanted Fibrosarcoma by Aroylhydrazone Analogs of the Gly-His-Lys-Cu(II) Complex," *Biochem. Pharmacol.* 32(24):3868–3871, 1983.
Pickart et al., "Growth-Modulating Plasma Tripeptide May Function By Facilitating Copper Uptake Into Cells," *Nature* 288:715–717, 1980.
"Newsreport on Use of GGH-Cu(II) and Ascorbic Acid," 1986, p. 38 Natural Healing Annual (M. Bricklin (ed.), Prevention Magazine, Rodale Press, Emmaus, Pa.).
Pickart et al., "A Synthetic Tripeptide which Increases Survival of Normal Liver Cells, and Stimulates Growth in Hepatoma Cells," *Biochem. Biophys. Res. Commun.* 54(2):562–66, 1973.
Aonuma et al., "Studies on Anti-ulcerogenic Protein in Inflamed Rabbit Skin Tissues," *Yakugaku Zasshi* 104(4):362–73, 1984.
Downey et al., "Acceleration of Wound Healing using GHL-Cu(II)," *Surgical Forum* 36:573–75, 1985.
Pickart et al., "A Human Plasma Growth Factor with Superoxide Dismatuse-like and Wound-healing Properties," Superoxide Dim. Chem. Biol. Med. Proc. Int. Conf. 4th 1985 (Pub. 1986), 555–57 (cited in *Chem. Abstracts* 106:13579c).
Frater-Schroder et al., "Tumor Necrosis Factor Type α, a Potential Inhibitor of Endothelial Cell Growth in vitro is Angiogenic in vivo," *Proc. Natl. Acad. Sci. USA* 34:5277–81, 1987.
Pickart, "The Use of Glycylhistidyllysine in Culture Systems," *In Vitro* 17(6):459–66, 1981.

*Primary Examiner*—Lester L. Lee
*Attorney, Agent, or Firm*—Seed and Berry

[57] ABSTRACT

Methods for the use of compositions of copper(II) containing compounds to accelerate healing of wounds in warm-blooded animals. The methods include systemic loading of copper(II) to accelerate the rate of wound healing following injury or surgery. The copper(II) containing compounds include copper(II) complexes with amino acids and peptides, and copper(II) salts.

1 Claim, No Drawings

5,164,367

METHOD OF USING COPPER(II) CONTAINING COMPOUNDS TO ACCELERATE WOUND HEALING

TECHNICAL FIELD

The present invention relates in general to the use of compositions of copper(II) containing compounds to accelerate healing of wounds in warm-blooded animals, and more specifically to systemic loading of copper(II) compounds to accelerate the rate of wound healing following injury or surgery to warm-blooded animals.

BACKGROUND OF THE INVENTION

Wound healing and tissue repair in humans and other warm-blooded animals are often inadequate or unacceptably slow. This is especially true in certain chronic diseases such as diabetes in the elderly, and in cancer patients. Chronic non-healing wounds create serious medical problems with infections, pain, extended hospitalization, and costly treatment.

Wound healing is a very complex process which involves the following phases or events. The first phase involves the recruitment of the proper types of white blood cells to cleanse the wound and initiate the healing response. The body seals off blood flow into the area and a white cell type called "neutrophilis" secrete toxic molecules (such as superoxide anion) into the wound to kill bacteria and induce a general inflammation.

The second phase involves the formation of granulation tissue (a mixture of fibroblasts, macrophages and new blood vessels in a loose matrix of collagen and other material) and the suppression of the inflammatory response. This occurs while while macrophages, monocytes, and other white blood cells invade to clean up tissue debris and open a path for mast cells and fibroblasts to follow and secrete angiogenic factors to attract capillary endothelial cells. There is a great proliferation of fibroblasts that secrete the structural protein collagen and glycosaminoglycans into the wound area. Reepithelialization of skin surface wounds will also commence early in the second phase.

The third and final stage involves the remodeling and formation of new connective tissue components, and wound closure.

A variety of approaches have been pursued to develop materials and methods which will aid in the healing process in warm blooded animals. One approach for the treatment of chronic wounds and skin ulcers has been the topical application of protein growth factors to the wound area (G. L. Brown et al., *N Eng. J. Med.*, 321:76–79, 1989). Other methods include the topical application of vasoactive peptides (P. A. Janssen, *J. Am. Acad. Dermatol.*, 21:85–90, 1989) and the systemic administration of macrophage activating agents such as tetachlorodecaoxygen (R. A. Hatz et al., *Plast. and Reconst. Surg.*, 84:953–959, 1989). In addition, certain peptide and peptide-derivative copper(II) complexes have been shown to accelerate wound healing in animals when applied topically or by injection at the locality of the wound (U.S. Pat. Nos. 4,665,054, 4,760,051, 4,810,693 and 4,877,770).

However, even though these compounds have shown positive results in wound healing, there still exists a need in the art for compositions and methods which accelerate the healing of wounds in warm-blooded animals.

SUMMARY OF THE INVENTION

Briefly stated, the present invention discloses methods and compositions for the treatment of wounds with copper(II) (i.e., $Cu^{2+}$) containing compounds in combination with a pharmaceutically acceptable carrier or diluent. The methods include systemic administration of a therapeutically effective amount of a composition containing copper(II) compounds. The methods are particularly useful to accelerate the rate of wound healing following injury or surgery in warm-blooded animals.

Adminstration of compositions of the present invention may be accomplished in any manner which will result in a systemic dose of copper(II) to the animal. For example, such administration may be injection (intramuscular, intravenous, subcutaneous or intradermal), oral, nasal, or suppository applications. Typically, compositions of the present invention include copper(II) containing compounds in solution for various forms for injection, or in pharmaceutical preparations which are formulated for the sustained release of the copper(II) compounds for oral, nasal, or suppository dosage application. The balance of the composition or pharmaceutical preparation comprises an inert, physiological acceptable carrier. Preferably, this carrier does not interact with the effectiveness of the copper(II) compounds.

Compounds of the present invention include copper(II) compounds that are capable of delivering copper(II) by systemic application. Such compounds include copper(II) complexed with naturally occuring substances such as amino acids, including glycine, alanine, valine, lysine, histidine, arginine, trytophan, phenylalanine, serine, leucine, isoleucine, proline, or any other naturally occurring amino acids. In addition to naturally occurring amino acids, a number of other substances may similarly be complexed to copper(II), including amino acid derivatives such as 3-methyl-histidine, and organic compounds such as citrate. Preferably, copper(II) complexes of the present invention bind copper(II) in such a manner that, after systemic administration, the copper(II) may be exchanged with binding sites in the body of the warm-blooded animal. For example, the binding sites for copper of bovine serum albumin (BSA).

Compounds of the present invention also include combinations of two or more amino acids or amino acid derivatives complexed with copper(II), such as the naturally occuring dipeptide β-alanyl-histidine (i.e., carnosine). Compounds of the present invention also include copper(II) complexed with, for example, glycyl-glycine, glycyl-glycyl-glycine, alanyl-(3-methyl)-histine, histidyl-valine, valyl-histidine, glycyl-serine, leucyl-glycine, phenylalanine-glycine, arginine-lysyl-glycine, histidyl-serine, lysyl-alanine and tyrosyl-lysine.

In yet another embodiment, compounds of the present invention include copper(II) salts, such as copper(II) sulfate, copper(II) acetate, and copper(II) chloride.

In addition, compounds of the present invention also include copper:peptide and copper peptide derivative complexes of the following general formulas designated A through I:

[glycyl-L-histidyl-L-lysine-R]:copper(II)         A wherein R is an aminoalkyl moiety containing from 1 to 18 carbon atoms, or is L-tryptophan, $(glycyl)_y$-L-tryptophan, where $y = 1$–4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a —$CH_2$— or —CH(OH)— moiety and n=4-20, or —$(X_4)_n$, where $X_4$ is a naturally occurring carbohydrate such as glucose, mannose, galactose, glucosamine or galactosamine and n=1-5;

[glycyl-$R_1$-$R_2$-$R_3$]:copper(II)    B wherein $R_1$ is selected from the group consisting of L-histidyl, L-(3-W)-histidyl and L-(5-W)-histidyl, where W is an alkyl moiety containing from 1 to 12 carbons atoms or aryl moiety containing from 6-12 carbon atoms;

$R_2$ is —$NHCH((CH_2)_nNH_3^+)CO$— where n=5-10; and $R_3$ is —$NH_2$, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a —$CH_2$— or —CH(OH)— moiety and n=4-20, or —$(X_4)_n$, where $X_4$ is a naturally occurring carbohydrate such as glucose, mannose, galactose, glucosamine or galactosamine and n=1-5;

[glycyl-$R_1$-$R_2$-$R_3$]:copper(II)    C wherein $R_1$ is selected from the group consisting of L-(3-W)-histidyl and L-(5-W)-histidyl where W is an alkyl moiety containing from 1 to 12 carbons atoms or aryl moiety containing from 6-12 carbon atoms;

$R_2$ is L-lysyl; and $R_3$ is —$NH_2$, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a —$CH_2$— or —CH(OH)— moiety and n=4-20, or —$(X_4)_n$, where $X_4$ is a naturally occurring carbohydrate such as glucose, mannose, galactose, glucosamine or galactosamine and n=1-5;

[glycyl-$R_1$-$R_2$-$R_3$]:copper(II)    D wherein $R_1$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_2$ is a basic amino acid such as arginine, a basic amino moiety such as cadaverine, spermine or spermidine, or a modified basic amino acid such as caprolactone; and $R_3$ is hydrogen, —$NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a —$CH_2$— or —CH(OH)— moiety and n=4-20, or —$(X_4)_n$, where $X_4$ is a naturally occurring carbohydrate such as glucose, mannose, galactose, glucosamine or galactosamine and n=1-5;

[$R_1$-$R_2$-glycine-$R_3$]:copper(II)    E wherein $R_1$ is L-lysyl or —$NHCH((CH_2)_nNH_3^+)CO$— where n=5-10;

$R_2$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms; and $R_3$ is hydrogen, —$NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a —$CH_2$— or —CH(OH)— moiety and n=4-20, or —$(X_4)_n$, where $X_4$ is a naturally occurring carbohydrate such as glucose, mannose, galactose, glucosamine or galactosamine and n=1-5;

[$R_1$-$R_2$-$R_3$-$R_4$]:copper(II)    F wherein $R_1$ is L-lysyl or —$NHCH((CH_2)_nNH_3^+)CO$— where n=5-10;

$R_2$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_3$ is a basic amino acid such as arginine, an amino moiety such as cadaverine, spermine or spermidine, or a modified basic amino acid such as caprolactone; and $R_4$ is hydrogen, —$NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6- 12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a —$CH_2$— or —CH(OH)— moiety and n=4-20, or —$(X_4)_n$, where $X_4$ is a naturally occurring carbohydrate such as glucose, mannose, galactose, glucosamine or galactosamine and n=1-5;

[$R_1$-glycyl-$R_2$-$R_3$]:copper(II)    G wherein $R_1$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_2$ is L-lysyl, —$NHCH((CH_2)_nNH_3^+)CO$—, where n=5-10, or a basic amino acid such as arginine, an amino moiety such as cadaverine, spermine or spermidine, or a modified basic amino acid such as caprolactone; and $R_3$ is hydrogen, $-NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a $-CH_2-$ or $-CH(OH)-$ moiety and n=4-20, or $-(X_4)_n$, where $X_4$ is a naturally occurring carbohydrate such as glucose, mannose, galactose, glucosamine or galactosamine and n=1-5;

$$[\text{L-alanyl-}R_1\text{-}R_2\text{-}R_3]:\text{copper(II)} \qquad H$$

wherein $R_1$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_2$ is L-lysyl or $-NHCH((CH_2)_nNH_3^+)CO-$ where n=5-10; and $R_3$ is $-NH_2$, an aminoalkyl moiety containing from 1 to 18 carbon atoms, or is L-tryptophan, (glycyl)$_y$-L-tryptophan, where y=1-4. L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a $-CH_2-$ or $-CH(OH)-$ moiety and n=4-20, or $-(X_4)_n$, where $X_4$ is a naturally occurring carbohydrate such as glucose, mannose, galactose, glucosamine or galactosamine and n=1-5; and $$[\text{glycyl-}R_1\text{-}R_2\text{-}R_3]:\text{copper(II)} \qquad I$$

wherein $R_1$ is L-lysyl or $-NHCH((CH_2)_nNH_3^+)CO-$ where n=5-10

$R_2$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms; and $R_3$ is hydrogen, $-NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a $-CH_2-$ or $-CH(OH)-$ moiety and n=4-20, or $-(X_4)_n$, where $X_4$ is a naturally occurring carbohydrate such as glucose, mannose, galactose, glucosamine or galactosamine and n=1-5.

In another embodiment of the present invention, an additional chelating agent may be added to the copper:-peptide complex to form a ternary metal:peptide:chelating agent complex. Suitable chelating agents include imidazole and imidazole containing compounds, such as histidine, and sulfur-containing amino acids, such as cysteine and methionine.

Methods of the present invention include the systemic administration to the warm-blooded animal of a therapeutically effective amount of a composition which includes a copper(II) containing compound of the present invention. Any pharmaceutically acceptable form of copper(II) compound may be used in the method of this invention. The method results in a loading of a therapeutic amount of copper(II) in the animal resulting in the acceleration of wound healing.

Other aspects of the present invention will become evident upon reference to the following detailed description.

DETAILED DISCRIPTION OF THE INVENTION

The present invention discloses compositions which accelerate the healing of wounds, lesions, surgical incisions, and other hard or soft tissue defects in warm-blooded animals. The invention also discloses methods for the general enhancement or acceleration of wound healing by the systemic administration of compositions or pharmeceutical preparations containing copper(II) compounds of the present invention.

Compositions containing copper(II) compounds can be liquids with inert ingredients or pharmaceutical preparations comprising a slow release form of copper-(II) compounds and suitable inert ingredients or pharmaceutical preparations for either oral, nasal, suppository, or parenteral applications. These pharmaceutical preparations can be prepared according to methods well known in the art.

Administration of compositions of the present invention may be accomplished in any manner which will result in a systemic dose of copper(II) to the animal. For example, such administration may be by injection (intramuscular, intravenous, subcutaneous or intradermal), oral, nasal, or suppository applications. Typically, compositions of the present invention include copper(II) containing compounds in solution for various forms for injection, or in pharmaceutical preparations which are formulated for the sustained release of the copper(II) compounds for oral, nasal, or suppository dosage application. The balance of the composition or pharmaceutical preparation comprises an inert, physiological acceptable carrier. Preferably, this carrier does not interact with the effectiveness of the copper(II) compounds.

Copper(II) containing compounds of the present invention accelerate healing throughout the animal and need not be administered directly to the damaged or afflicted tissue. Rather, acceleration of wound healing in internal wounds is achieved by systemic administration of the copper(II) containing compound. Many wounds are too deep or are too irregular to treat adequately by local administration of healing agents. It is also difficult to administer healing agents to wounds remaining after internal surgery of bone repair. Systemic administration permits the copper(II) containing compounds of the present invention to be transported to the wound site via the blood vessel network, thus permitting a natural delivery of the copper(II) compounds to the cell and tissues.

Compounds of the present invention include copper-(II) compounds that are capable of delivering copper-(II) by systemic application. Such compounds include copper(II) complexed with naturally occuring substances such as amino acids, including glycine, alanine, valine, lysine, histidine, arginine, trytophan, phenylalanine, serine, leucine, isoleucine, proline, or any other naturally occurring amino acids. In addition to naturally occurring amino acids, a number of other substances may similarly be complexed to copper(II), including amino acid derivatives such as 3-methyl-histidine, and organic compounds such as citrate. Preferably, copper(II) complexes of the present invention are capable of binding copper(II) in such a manner that after systemic administration, the copper(II) may be exchanged with binding sites in the body of the warm-blooded animal, such as, for example, the binding site for copper of BSA.

Compounds of the present invention also include combinations of two or more amino acids or amino acid derivatives complexed with copper(II), such as the naturally occuring dipeptide $\beta$-alanyl-histidine (i.e., carnosine). Compounds of the present invention also include copper(II) complexed with, for example, glycyl-glycine, glycyl-glycyl-glycine, alanyl-(3-methyl)-histidine, histidyl-valine, valyl-histidine, glycyl-serine, leucyl-glycine, phenylalanine-glycine, arginine-lysyl-glycine, histidyl-serine, lysyl-alanine and tyrosyl-lysine.

In yet another embodiment, compounds of the present invention include copper(II) salts, such as copper(II) sulfate, copper(II) acetate, and copper(II) chloride.

In still another embodiment, compounds of the present invention include the complexes of the general formula designated A through I above. For example, in Formula F if $R_1$ is L-lysyl, $R_2$ is L-histidyl, $R_3$ is arginine, $R_4$ is an n-octyl alkoxy moiety, and the metal is copper(II), the structure of the copper(II):peptide complex would be as follows:

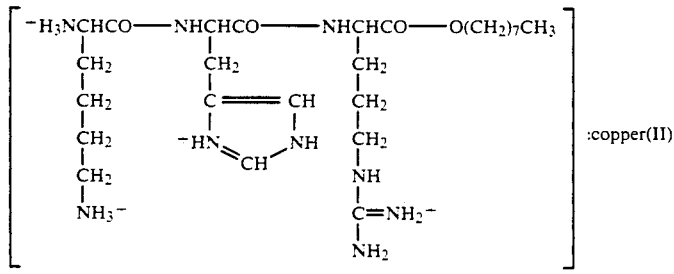

Similarly, if $R_4$ were an aminoalkyl moiety containing three carbon atoms of the formula $-NH(CH_2)_2CH_3$, the metal:peptide complex would have the following structure:

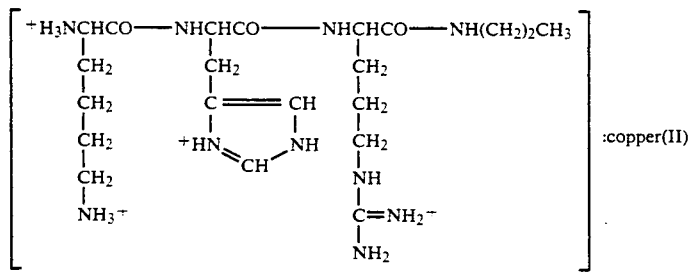

The chiral amino acids of the present invention have been designated as the L form. However, one skilled in the art would readily appreciate that the D forms of the amino acids may be utilized as a substitute for the L forms.

It will be recognized to one skilled in the art that compounds of the present invention also include penicillamine, ethylenediaminetetraacetic acid, desserrox-amine, and other copper(II) chelating agents complexed with copper(II).

The ability of a chelating agent to bind copper(II) is typically expressed as a "log K" binding or stability constant (Martell et. al., *The Determination and Use of Stability Constants*, V.C.H. Publishers Inc, New York, N.Y., 1988, incorporated herein by reference). Preferably, the copper(II) containing compounds of the present invention possess a log K binding constant for copper(II), at physiological pH, less than the binding constant of EDTA for copper(II). Chelating agents with binding constants equal to or greater than EDTA bind copper(II) too tightly, and thus will not exchange the copper with the binding sites in the body of the warm-blooded animal.

The peptides of the present invention may be synthesized either by solution chemical techniques or by solid phase techniques. The general procedure involves the stepwise addition of protected amino acids to build up the desired peptide sequence. Such methodology is well known to those skilled in the art. Illustrative syntheses of complexes of the present invention are presented in the examples hereinbelow.

Within the present invention, one may utilize a molar ratio of peptide or amino acid to copper(II) of, for example, 1:1, 2:1 or greater (e.g., 3:1). Preferably, the peptide or amino acid to copper(II) molar ratio is 2:1.

In another embodiment of the present invention, a chelating agent may be added to the copper(II):peptide complex to form a ternary copper(II):peptide:chelating agent complex. Suitable chelating agents include imidazole or imidazole-containing compounds, such as histidine, and sulfur containing amino acids, such as cysteine or methionine. Thus, if the copper(II):peptide complex is glycyl-L-histidyl-L-lysine:copper(II), histidine may be added to yield the ternary complex glycyl-L-histidyl-L-lysine:copper(II):histidine. However, to form such a ternary complex, the molar ratio of copper(II) to peptide to chelating agent must be considered. For example, if the ratio of peptide to copper(II) is 2:1, the addition of a chelating agent to the copper(II):peptide complex, although possible, is difficult due to site occupancy by the peptide. However, by maintaining the ratio of peptide to copper(II) near 1:1, a chelating group may readily be added to form the ternary complex. Preferably, the peptide to copper(II) to chelating agent ratio is 1:1:1.

Compositions or pharmaceutical preparations of the present invention may contain suitable inert ingredients for either oral or parenteral applications (i.e., pharmaceutically acceptable carriers). The diluent or carrier should not interact with the copper(II) containing compound to significantly reduce the effectiveness thereof.

Methods for encapsulating compositions (such as in a coating of hard gelatin) for oral or suppository administration are well known in the art (Baker et al., *Controlled Release of Biological Active Agents*, John Wiley and Sons, 1986, incorporated herein by reference). Suitable pharmaceutically acceptable carriers for parenteral application, such as intravenous, subcutaneous or intramuscular injection, include sterile water, physiological saline, bacteriostatic saline (saline containing 0.9 mg/ml benzyl alcohol) and phosphate-buffered saline.

Compositions of the present invention may be administered either orally or nasally, by suppository, or by injection either intravenously, subcutaneously, intramuscularly, or intradermally.

The balance of the compositions or pharmaceutical preparations comprises an inert, physiological acceptable carrier. This carrier should not interact with the active ingredients nor reduce the effectiveness of the copper(II) compounds. Suitable carriers include, but are not limited to, water, physiological saline, bacteriostatic saline (saline containing 0.9 mg/ml benzyl alcohol), and phosphate buffered saline.

An effective dosage of compositions or pharmaceutical preparations of the present invention delivers approximately 0.01 to 20 mg of copper(II) containing compound per kg body weight. The required dosage will vary according to the particular condition to be treated, the severity of the condition, and the duration of the treatment.

The following examples are offered by way of illustration, and not by way of limitation.

EXAMPLES

To summarize the examples that follow, Examples 1-9 illustrate the synthesis of representative copper(II) containing compounds of the present invention; Examples 10-17 illustrate the stimulation of wound healing by representative copper(II) containing compounds of the present invention.

Specifically, Example 1 illustrates the preparation of copper(II) peptide complexes. Example 2 illustrates the synthesis of glycyl-L-histidyl-L-lysine n-octyl ester copper(II). Example 3 illustrates the synthesis of glycyl-L-histidyl-L-lysine n-octyl amide. Example 4 illustrates the synthesis of glycyl-L-histidyl-L-lysyl-L-valyl-L-phenylalanyl-L-valine. Example 5 illustrates the synthesis of L-alanyl-L-histidyl-L-lysine. Example 6 illustrates the synthesis of L-lysyl-L-histidyl-L-glycine. Example 7 illustrates the synthesis of L-lysyl-L-histidyl-L-glycyl-L-valyl-L-phenylalanyl-L-valine. Example 8 illustrates the synthesis of glycyl-L-histidy-L-caprolactam. Example 9 illustrates the synthesis of L-histidyl-glycyl-L-lysine.

Example 10 illustrates the stimulation of wound healing by intramuscular (I.M.) injection of glycyl-L-histidyl-L-lysine:copper(II). Example 11 illustrates the stimulation of wound healing in healing impaired rats by I.M. injection of glycyl-L-histidyl-L-lysine:copper(II). Example 12 illustrates the stimulation of wound healing by I.M. injection of glycyl-L-histidyl-L-lysyl-L-valyl-L-phenylalanyl-L-valine:copper(II). Example 13 illustrates the stimulation of wound healing in healing impaired animals by I.M. injection of copper(II) compounds. Example 14 illustrates the stimulation of wound healing in mice by I.M. injection of glycyl-L-histidyl-L-lysine:copper(II). Example 15 illustrates the stimulation of wound healing in pigs by I.M. injection of glycyl-L-histidyl-L-lysine:copper(II). Example 16 illustrates the stimulation of wound healing by hydrophobic and albumin binding derivatives of glycyl-L-histidyl-L-lysine:copper(II). Example 17 illustrates the stimulation of healing by sequence variations of glycyl-L-histidyl-L-lysine:copper(II).

Source of Chemicals

Chemicals and peptide intermediates utilized in the following examples may be purchased from a number of suppliers, for example: Sigma Chemical So., St. Louis, Mo.; Peninsula Laboratories, San Carlos, Calif.; Aldrich Chemical Company, Milwaukee, Wis.; Vega Biochemicals, Tucson, Ariz.; Pierce Chemical Co., Rockford, Ill.; Research Biochemicals, Cleveland, Ohio; Van Waters and Rogers, South San Francisco, Calif.; and Bachem, Inc., Torrance, Calif.

EXAMPLE 1

Preparation of Copper(II):Peptide Complexes

The copper(II):peptide complexes of the present invention may be synthesized by dissolving the peptide in distilled water, followed by the addition of purified copper(II) chloride and a then adjusting the pH of the solution. For example, copper(II) complexes of glycyl-L-histidyl-L-lysine ("GHL") with a molar ratio of peptide to copper(II) of 1:1, 2:1, or greater (e.g., 3:1), may be prepared by dissolving a given weight of GHL in distilled water (e.g., 50 mg/ml), and adding the desired molar amount of purified copper(II) chloride. The pH of the resulting peptide solution is then adjusted to about 7.0 by the addition of a sodium hydroxide solution. Alternatively, copper(II) salts other than the copper(II) chloride may be utilized, such as copper(II) acetate or copper(II) sulfate.

EXAMPLE 2

Synthesis of Glycyl-L-Histidyl-L-Lysine Octyl Ester:Copper (II)

A mixture of $N^e$-benzyloxycarbonyl-L-Lysine, n-octanol, benzene, and p-toluenesulfonic acid monohydrate was refluxed overnight using a Dean-Stark trap to remove water. After cooling, dry ethyl ether was added. The solution was then allowed to precipitate at 0° C. overnight. A portion of the precipitate solid was added to 50 ml of potassium carbonate solution and 50 ml of dichloromethane. After extraction, the layers were separated and the organic phase was washed with water and brine, then dried with anhydrous magnesium sulfate. Filtration, evaporation and purification by flash column chromatography gave n-octyl $N^e$-benzyloxycarbonyl-L-lysinate.

The product was dissolved in tetrahydrofuran and mixed with $N^a$-t-butyloxycarbonyl-$N^{im}$-benzyloxycarbonyl-L-histidine, isobutyl chloroformate and N-methylmorpholine. After evaporation, water and ethyl acetate were added. The product was extracted into the organic phase, which was dried with anhydrous magnesium sulfate. Filtration, evaporation, and purification by flash column chromatography gave n-octyl $N^a$-t-butyloxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-octyl $N^{im}$-benzyloxycarbonyl-L-histidyl-$N^e$-benzyloxycarbonyl-L-lysinate. This was dissolved in tetrahydrofuran, and isobutyl chloroformates, N-methylmorpholine and benzyloxycarbonylglycine were added to form n-octyl benzyloxycarbonylglycyl-$N^{im}$-benzyloxycarbonyl-L-histidyl-$N^e$-benzyloxycarbonyl-L-lysinate. This was dissolved in glacial acetic acid and hydrogenated overnight in the presence of 10% Pd-C catalyst.

The resultant n-octyl ester of glycyl-L-histidyl-L-lysine was converted to the copper(II) complex by dissolving water and mixing with equimolar copper(II) acetate. The pH was raised to neutrality with sodium hydroxide. The solution was centrifuged at 20,000 C g for 1 hour at 3° C. to remove poorly soluble material. The supernatant solution was lyophilized to obtain glycyl-L-histidyl-L-lysine n-octyl ester:copper(II).

EXAMPLE 3

Synthesis of Glycyl-L-Histidyl-L-Lysine N-Octylamide

A solution of $N^a$-t-butyloxycarbonyl-$N^e$-benzyloxycarbonyl-L-lysine in tetrahydrofuran was treated with N-methyl-morpholine, isobutyl chloroformate, and octylamine at −15° C. The resulting fully protected octyl amide was then treated with 50% trifluoroacetic acid in dichloromethane at room temperature, neutralized with saturated aqueous potassium bicarbonate solution, and extracted into ethyl acetate. Evaporation gave the deblocked lysinamide which was added to a solution prepared from $N^a$-t-butyloxycarbonyl-$N^{im}$-benzyloxycarbonyl-L-histidine, N-methylmorpholine, and isobutyl chloroformate in dry tetrahydrofuran at −15° C.

The fully protected dipeptide formed above was deblocked by treatment with 50% trifluoroacetic acid in dichloromethane at room temperature followed by neutralization with saturated aqueous potassium bicarbonate. Extraction into ethyl acetate and evaporation gave the partially deblocked dipeptide, which was added to a solution prepared from benzyloxycarbonyl glycine, N-methylmorpholine, and isobutyl chloroformate in dry tetrahydrofuran at −15° C. The resulting protected tripeptide was deblocked by treatment with hydrogen in the presence of 10% palladium on carbon in glacial acetic acid. Filtration and lyophilization gave glycyl-L-histidyl-L-lysine n-octyl amide as its triacetate salt.

EXAMPLE 4

Synthesis of Glycyl-L-Histidyl-L-Lysyl-L-Valyl-L-Phenylalanyl-L-Valine

Glycyl-L-histidyl-L-lysyl-L-valyl-L-phenylalanyl-L-valine was synthesized by standard solution phase method using t-butyloxycarbonyl protecting group for the alpha nitrogen, benzyloxycarbonyl group for side-chain protection and mixed anhydride method for coupling. Briefly stated, L-valine benzyl ester p-toluenesulfonate salt was coupled with t-butyloxycarbonyl-L-phenylalanine using isobutyl chloroformate and N-methylmorpholine as a coupling agent (2 hours at −20° C., then 1 hour at ambient temperature). The t-butyloxycarbonyl protecting group of the dipeptide was then removed by 30% trifluoroacetic acid in dichloromethane at room temperature for 30 minutes. Blocked amino acids (t-butyloxycarbonyl-L-valine, $N^a$-t-butyloxycarbonyl-$N^e$-benzyloxycarbonyl-L-lysine, $N^a$-t-butyloxycarbonyl-$N^{im}$-benzyloxycarbonyl-L-histidine, benzyloxycarbonylglycine) were added in sequential order, and t-butyloxycarbonyl protecting groups were removed to obtain the desired peptide. The final peptide was completely deprotected using hydrogen gas in acetic acid for 5 days in the presence of 10% Pd-C catalyst. The final peptide was lyophilized from water to obtain the tri-acetate salt.

EXAMPLE 5

Synthesis of L-Alanyl-L-Histidyl-L-Lysine $N^e$-benzyloxycarbonyl-L-lysine benzyl ester hydrochloride salt was suspended in tetrahydrofuran (THF) and coupled with $N^a$-t-butyloxycarbonyl-$N^{im}$-benzyloxycarbonyl-L-histidine using isobutyl chloroformate and N-methylmorpholine (2 equivalents) in THF. After two hours at −20° C. and an additional hour at ambient temperature, the reaction was quenched with 2N aqueous potassium bicarbonate. The product was extracted into ethyl acetate, washed with 1M aqueous citric acid, and saturated sodium bicarbonate. The organic phase was dried over anhydrous sodium sulfate. Filtration and evaporation gave benzyl $N^a$-t-butyloxycarbonyl-$N^{im}$-benzyloxycarbonyl-L-histidyl-$N^e$-benzyloxycarbonyl-L-lysinate.

The product was dissolved in 30% trifluoroacetic acid in dichloromethane for 30 minutes, then evaporate, forming benzyl $N^{im}$-benzyloxycarbonyl-L-histidyl-$N^e$-benzyloxycarbonyl-L-lysinate. This was dissolved in tetrahydrofuran, and isobutyl chloroformate, N-methyl-morpholine and benzyloxycarbonylalanine were added to form benzyl benzyloxycarbonylalanyl-$N^{im}$-benzyloxycarbonyl-L-histidyl-$N^e$-benzyloxycarbonyl-L-lysinate. This product was then dissolved in acetic acid and hydrogenated overnight in the presence of 10% Pd-C catalyst. The resultant alanyl-L-histidyl-L-lysine was lyophilized from water several times to yield the desired tripeptide as a diacetate salt.

EXAMPLE 6

Synthesis of L-Lysyl-L-Histidyl-Glycine $N^a$-t-butyloxycarbonyl-$N^{im}$-benzyloxycarbonyl-L-histidine was dissolved in tetrahydrofuran (THF) and neutralized with one equivalent of N-methylmorpholine. It was then coupled with benzyl glycinate p-toluenesulfonate salt using isobutyl chloroformate and N-methylmorpholine. After two hours at −20° C. and an additional hour at ambient temperature, the reaction was quenched with 2N aqueous potassium bicarbonate. The product was extracted into ethyl acetate, washed with 1M aqueous citric acid, and saturated sodium bicarbonate. The organic phase was dried over anhydrous sodium sulfate. Filtration and evaporation gave benzyl $N^a$-t-butyloxycarbonyl-$N^{im}$-benzyloxycarbonyl-L-histidyl-glycinate.

This product was dissolved in anhydrous methanolic hydrogen chloride (saturated at 0° C.) for 5 minutes, followed by removal of solvent under reduced pressure, forming benzyl $N^{im}$-benzyloxycarbonyl-L-histidyl-glycinate. This was dissolved in tetrahydrofuran, and isobutyl chloroformate, N-methylmorpholine and $N^a,N^e$-dibenzyloxycarbonyl-L-lysine were added to form benzyl $N^a,N^e$-dibenzyloxycarbonyl-L-lysyl-$N^{im}$-benzyloxycarbonyl-L-histidyl-glycinate (3 hours at −20° C., the 1 hour at ambient temperature). This product was then dissolved in methanol/acetic acid, 1:1 (v/v), and hydrogenated overnight in the presence of 10% Pd-C catalyst. The resultant L-lysyl-L-histidyl-glycine was lyophilized from water several times, then purified by liquid chromatography on a C-18 reverse-phase column to yield the desired tripeptide triacetate salt as a foamy white solid.

EXAMPLE 7

Synthesis of L-Lysyl-L-Histidyl-Glycyl-L-Valyl-L-Phenylalanyl-L-Valine

L-lysyl-L-histidyl-glycyl-L-valyl-L-phenylalanyl-L-valine was synthesized by standard solution phase method using t-butyloxycarbonyl protecting group for the alpha nitrogen, benzyloxycarbonyl group for side-chain protection and mixed anhydride method for coupling. Briefly stated, L-valine benzyl ester p-toluenesulfonate salt was coupled with t-butyloxycarbonyl-L-phenylalanine using isobutyl chloroformate and N-methylomorpholine as coupling agent (2 hours at −20° C., then 1 hour at ambient temperature). The t-butyloxycarbonyl protecting group of the dipeptide was then removed by 30% trifluoroacetic acid in dichloromethane at room temperature for 30 minutes. Blocked amino acids (t-butyloxycarbonyl-L-valine, t-butyloxycarbonylglycine, $N^a$-t-butyloxycarbonyl-$N^{im}$-benzyloxycarbonyl-L-histidine, $N^a$, $N^e$-dibenzyloxycarbonyl-L-lysine) were added in sequential order and t-butyloxycarbonyl protecting groups were removed to obtain the desired peptide. The final peptide was completely deprotected using hydrogen gas in glacial acetic acid for five days in the presence of 10% Pd-C catalyst. The final peptide was lyophilized from water and purified by liquid chromatography on a C-18 reverse phase column to produce the desired hexapeptide in multi-gram quantity.

The above systematic synthesis proved advantageous over some of the solid phase methods in providing multi-gram quantity of the desired peptide in high purity with minimal purification.

EXAMPLE 8

Synthesis of Glycyl-L-Histidyl-L-Caprolactam

L(−)-3-amino-e-caprolactam was dissolved in tetrahydrofuran (THF) then coupled with $N^a$-t-butyloxycarbonyl-$N^{im}$-benzyloxycarbonyl-L-histidine using isobutyl chloroformate and N-methylmorpholine in THF. After two hours at −20° C. and an additional hour at ambient temperature, the reaction was quenched with 2N aqueous potassium bicarbonate. This produce was extracted into ethyl acetate, washed with 1M aqueous citric acid, and saturated sodium bicarbonate. The organic phase was dried over anhydrous sodium sulfate. Filtration and evaporation gave $N^a$-t-butyloxycarbonyl-$N^{im}$-benxyloxycarbonyl-L-histidyl-L-caprolactam.

The above protected dipeptide was dissolved in 30% trifluoroacetic acid in dichloromethane for 30 minutes, then evaporated, forming $N^{im}$-benzyloxycarbonyl-L-histidyl-L-caprolactam. This was then dissolved in tetrahydrofuran, and isobutyl chloroformate, N-methylmorpholine and benzyloxycarbonylglycine were added to form benzyloxycarbonylglycyl-$N^{im}$-benzyloxycarbonyl-L-histidyl-L-caprolactam. This product was re-crystallized once from ethyl acetate then dissolved in acetic acid and hydrogenated overnight in the presence of 10% Pd-C catalyst. The resultant glycyl-L-histidyl-L-caprolactam was lyophilized from water several times, then purified by liquid chromatography on a C-18 reverse-phase column to yield the desired tripeptide as a diacetate salt.

EXAMPLE 9

Synthesis of L-Histidyl-Glycyl-L-Lysine $N^e$-benxyloxycarbonyl-L-lysine benzyl ester hydrochloride salt was suspended in tetrahydrofuran (THF) and coupled with $N^a$-t-butyloxycarbonylglycine using isobutyl chloroformate and N-methylmorpholine in THF. After two hours at −20° C. and an additional hour at ambient temperature, the reaction was quenched with 2N aqueous potassium bicarbonate. The produce was extracted into ethyl acetate, washed with 1M aqueous citric acid, and saturated sodium bicarbonate. The organic phase was dried over anhydrous sodium sulfate. Filtration and evaporation gave benzyl $N^a$-t-butyloxycarbonyl-glycyl-$N^e$-benzyloxycarbonyl-L-lysinate.

The product was dissolved in 30% trifluoroacetic acid in dichloromethane for 30 minutes, then evaporated, forming benzyl glycyl-$N^e$-benzyloxycarbonyl-L-lysinate. This was dissolved in tetrahydrofuran, and isobutyl chloroformate, N-methylmorpholine and $N^a$-benzyloxycarbonyl-$N^{im}$-benzyloxycarbonyl-L-histidine were added to form benzyl $N^a$-benzyloxycarbonyl-$N^{im}$-benzyloxycarbonyl-L-histidyl-glycyl-$N^e$-benzyloxycarbonyl-L-lysinate. This product was then dissolved in acetic acid and hydrogenated overnight in the presence of 10% Pd-C catalyst. The resultant L-histidyl-glycyl-L-lysine was lyophilized from water several times to yield the desired tripeptide as a diacetate salt.

EXAMPLE 10

Stimulation of Wound Healing by I.M. Injection of Glycyl-Histidyl-Lysine:Copper(II)

The subcutaneous implantation of stainless steel wound chambers in rats provides a model for the healing of open cavity wounds. This model in many ways mimics the early events in the formation of granulation tissue found in many types of wounds and surgical defects. Implantation of these chambers triggers a series of responses which reflect the series of phases involved in wound healing—fibrin clot formation, infiltration of white cells, collagen synthesis, and new blood vessel formation.

The assay involves the implantation of two Stainless steel chambers (1×2.5 cm cylindrical 312 SS, 20 mesh, with Teflon end caps) on each side of the dorsal midline of rats. After one week to allow for encapsulation of the chambers, the animal was injected with a solution containing a copper(II) compound of the present invention. Controls consist of chambers injected with the same volume of saline. Injections were made on days 5,7,8,12,13,15,19. The chambers were removed at day 15 and 29.

The chambers were lyophylized and the interior contents removed for biochemical analysis. The biochemical parameters examined include the total dry weight, protein content, angiogenesis (Alkaline Phosphatase activity), and collagen content (Hydroxyproline content after acid hydrolysis). Significant increases have been found in all the biochemical parameters tested.

The protein was determined by the method of Lowry (J. Biol. Chem., 193:265-275, 1951) using Bovine Serum Albumin (BSA) as a standard. Angiogenesis was determined by measuring the amount of Alkaline Phosphatase using p-nitrophenyl phosphate as a substrate (G. Lyles et al., Biochem. Pharm., 33:2569-2574, 1984). The collagen content was determined by acid hydrolysis and a colormetric assay for hydroxyproline (I. Bergman, Clin. Chim. Acta, 27:347-349, 1970), an amino acid specific for collagen.

The total protein is expressed as mg protein (relative to BSA) per chamber. Angiogenesis is expressed as alkaline phosphate (AP) Units per chamber, where one Unit=the amount of homogenate which causes an increase in absorbance at 405 nm of 1.0 per min. The hydroxyproline (HP, Collagen Content) is expressed as $\mu$g HP per chamber.

After allowing for encapsulation of the chambers, the rats were injected I.M. with 0.1 ml of either a saline solution containing 10 mg/ml glycyl-L-histidyl-L-lysine:copper(II) (2:1 molar ratio) or saline. The chambers were harvested and the biochemical parameters of granulation tissue formation examined as described above. The I.M. injection of this compound significantly increased the biochemical healing parameters in the rats as summarized in Table 1.

for encapsulation of the chambers, the rats were injected I.M. (in the opposite leg from the cortisone injection) with 0.1 ml of either a saline solution containing 10 mg/ml of glycyl-L-histidyl-L-lysine:copper(II) (2:1 molar ratio) or saline. The chambers were harvested and the biochemical parameters of granulation tissue formation examined as described in Example 10.

The I.M. injection of glycyl-L-histidyl-L-lysine:copper(II) in the cortisone treated animals increased the level of all the biochemical parameters examined compared to the level found in the control animals. Moreover, I.M. treatment with the GHL-Cu increased the healing response in the healing impaired animals to the level found in the normal animals. The results of this experiment are presented in Table 2.

TABLE 2

| | EFFECT OF I.M. GHL-Cu ON WOUND HEALING IN HEALING IMPAIRED RATS | | | | |
|---|---|---|---|---|---|
| COMPOUND | DOSE mg/injection | DRY WEIGHT mg | PROTEIN mg/chamber | COLLAGEN $\mu$g HP/chamber | ANGIOGENESIS Units AP/chamber |
| HEALING IMPAIRED RATS | | | | | |
| SALINE | — | 20 ± 12 | 11 ± 8 | 187 ± 101 | 0.5 ± 0.3 |
| GHL-Cu | 1.0 | 35 ± 13 | 25 ± 9 | 366 ± 74 | 1.5 ± 1.6 |

NOTES TO TABLE 1:
GHL:Cu = glycyl-L-histidyl-L-lysine:copper(II)(2:1 Molar Complex)

EXAMPLE 12

Stimulation of Wound Healing by I.M. injection of Glycyl-Histidyl-Lysine-Valine-Phenylalanyl-Valine-Copper(II)

Groups of rats had wound chambers implanted as described in Example 10. After implantation of the chambers, the rats were subsequently injected with Cortisone Acetate (10 mg I.M. daily, Cortone Acetate, Merck) to impair the healing response. After allowing for encapsulation of the chambers, the rats were injected I.M. (in the opposite leg from the cortisone injection) with 0.1 ml of either a saline solution containing 19 mg/ml of glycyl-L-histidyl-L-lysyl-valyl-phenylalanly-valine:copper(II) or saline. The chambers were harvested and the biochemical parameters of granulation tissue formation examined as described in Example 10.

The I.M. injection of glycyl-L-histidyl-L-lysyl-valyl-phenylalanly-valine:copper(II) in the cortisone treated animals increased the level of all the biochemical parameters examined. This experiment is summarized in Table 3.

TABLE 1

| | EFFECT OF I.M. GHL-Cu ON WOUND HEALING IN RATS | | | | |
|---|---|---|---|---|---|
| COMPOUND | DOSE mg/injection | DRY WEIGHT mg | PROTEIN mg/chamber | COLLAGEN $\mu$g HP/chamber | ANGIOGENESIS Units AP/chamber |
| NORMAL RATS | | | | | |
| SALINE | — | 51 ± 15 | 36 ± 13 | 376 ± 86 | 2.2 ± 1.1 |
| GHL:Cu | 1.0 | 75 ± 25 | 55 ± 19 | 1273 ± 711 | 3.0 ± 1.5 |

NOTES TO TABLE 1:
GHL:Cu = glycyl-L-histidyl-L-lysine:copper(II)(2:1 Molar Complex)

EXAMPLE 11

Stimulation of Wound Healing in Healing Impaired Rats by I.M. Injection of Glycyl-Histidyl-Lysine:Copper(II)

Groups of rats had wound chambers implanted as described in Example 10. After implantation of the chambers, the rats were subsequently injected with Cortisone Acetate (10 mg I.M. daily, Cortone Acetate, Merck) to impair the healing response. After allowing

TABLE 3

| | EFFECT OF SYSTEMIC GHLVFV-Cu ON WOUND HEALING IN CORTISONE TREATED RATS | | | | |
|---|---|---|---|---|---|
| COMPOUND | DOSE mg/injection | DRY WEIGHT mg | PROTEIN mg/chamber | COLLAGEN $\mu$g HP/chamber | ANGIOGENESIS Units AP/chamber |
| SALINE | — | 65 ± 8 | 32 ± 4 | 502 ± 145 | 1.9 ± 0.4 |

TABLE 3-continued

EFFECT OF SYSTEMIC GHLVFV-Cu ON WOUND HEALING IN CORTISONE TREATED RATS

| COMPOUND | DOSE mg/injection | DRY WEIGHT mg | PROTEIN mg/chamber | COLLAGEN μg HP/chamber | ANGIOGENESIS Units AP/chamber |
|---|---|---|---|---|---|
| GHLVFV:Cu | 1.9 | 84 ± 28 | 45 ± 15 | 1279 ± 1001 | 6.9 ± 6.1 |

NOTES TO TABLE 1:
GHL:Cu = glycyl-L-histidyl-L-lysine:copper(II)(2:1 Molar Complex)
GHLVFV:Cu = glycyl-L-histidyl-L-lysyl-L-valyl-L-phenylalanyl-L-valine:copper(II)(2:1 Molar Complex)

EXAMPLE 13

Stimulation of Wound Healing in Healing Impaired Rats By I.M. Injection of Copper Compounds Groups of rats had wound chambers implanted as described in Example 10. After implantation of the chambers, the rats were subsequently injected with Cortisone Acetate (10 mg I.M. daily, Cortone Acetate, Merck) to impair the healing response. After allowing for encapsulation of the chambers, the rats were injected I.M. (in the opposite leg from the cortisone injection) with 0.1 ml of the copper(II) compounds listed at the dosage specified in Table 4, or saline. The chambers were harvested and the biochemical parameters of granulation tissue formation examined as described in Example 10.

The I.M. injection of these compounds in the cortisone treated animals increased the level of collagen (a major component of granulation tissue) accumulation above the control level found in the saline injected animals.

TABLE 4

EFFECTS OF COPPER COMPOUNDS ON WOUND HEALING IN HEALING IMPAIRED RATS

| COMPOUND | DOSE mg/injection | COLLAGEN μg HP/chamber |
|---|---|---|
| SALINE | — | 502 ± 145 |
| GGG:Cu | 0.3 | 829 ± 210 |
| CuSO4 | 0.2 | 976 ± 343 |
| CARN:Cu | 0.3 | 832 ± 174 |
| CITRATE:Cu | 0.5 | 976 ± 343 |

NOTES TO TABLE 4
GGG:Cu = glycyl-glycyl-glycine:copper(II)(2:1 Molar complex)
CuSO4 = cupric sulfate solution
CARN:Cu = carnosine:copper(II)(2:1 Molar complex)
CITRATE:Cu = citrate:copper(II)(2:1 Molar complex)

EXAMPLE 14

Stimulation of Wound Healing by I.M. Injection of Glycyl-Histidyl-Lysine:Copper(II) in Mice The ability of copper(II) containing compounds to accelerate wound healing in mice is demonstrated in a full thickness defect model. Following an acclimation period, mice are anesthetized with I.P. pentobarbital and prepped for surgery. The hair is plucked from a wide area of the mid-back. An ink stamp bearing a 15 mm diameter circle is used to mark the skin for subsequent full-thickness excision. Tissue is excised to the fascia underlying the paniculus carnosus muscle. Following excision, hemostasis is achieved through irrigation and the use of sterile gauze pads.

Mice received a first I.M. treatment of GHL-Cu following hemostasis, Day 0. Injections consisted of 0.1 mg of GHL-Cu in a volume of 0.1 ml. Mice used as controls received injections of saline. Injections were repeated on days 1, 2, 3, 6, 7, 8, 9, 10, and 13.

The residual wound surface area is measured on days 1, 7, 10 and 14. The final comparison is performed on Day 14. Table 5 below illustrates that I.M. injection of GHL-Cu resulted is an approximately 75% smaller residual wound size at 14 days.

TABLE 5

WOUND HEALING ACTIVITY OF GHL-Cu IN MICE AFTER I.M. INJECTION

| TREATMENT | RESIDUAL WOUND SURFACE AREA (SQ MM) DAY 14 |
|---|---|
| SALINE | 1.78 ± 2.56 |
| GHL:CU | 0.42 ± 0.60 |

NOTES TO TABLE 5:
GHL:Cu = glycyl-L-histidyl-L-lysine:copper(II)(2:1 Molar Complex)

EXAMPLE 15

Stimulation of Wound Healing in Pigs by I.M. Injection of Glycyl-Histidyl-Lysine: Copper(II)

The systemic application of GHL-Cu increases the formation of granulation tissue in pigs. Two domestic pigs approximately 29-31 pounds, about 8 weeks old, were anesthetized with Ketamine (30 mg/Kg) and Rompum (5 mg/Kg). A series of full thickness skin defects measuring 2.0×2.0 cm were created on the backs of each pig and bandaged with gauze and adhesive tape. One pig was treated with I.M. injections of sterile saline and the other with a solution of GHL-Cu (30 mg/ml). Each pig received 1.0 ml injections of either the saline or GHL-Cu solution on days 0, 1, 2, 5, 6, 7, 8, 9, 12, and 13.

Punch biopsy samples were taken from the centers of the healing wounds on day 7 and day 12 and analyzed for the biochemical parameters of granulation tissue and described in Example 10. The results show that there was a significant increase in the weight, collagen content, and angiogenesis in the biopsies from the GHL-Cu treated pig. The data from this experiment is summarized in Table 6 below. In addition, visual examination showed that the granulation tissue in the GHL-Cu treated pig was raised above the level of the surrounding skin, compared to a level below the skin for the saline treated animal.

TABLE 6

EFFECT OF I.M. GHL-Cu ON WOUND HEALING IN PIGS

| TREATMENT | DOSE mg/injection | WET WEIGHT mg | COLLAGEN μg HP/chamber | ANGIOGENESIS Units AP/chamber |
|---|---|---|---|---|
| SALINE | — | 121 ± 7 | 628 ± 182 | 0.4 ± 0.1 |

TABLE 6-continued

EFFECT OF I.M. GHL-Cu ON WOUND HEALING IN PIGS

| TREATMENT | DOSE mg/injection | WET WEIGHT mg | COLLAGEN μg HP/chamber | ANGIOGENESIS Units AP/chamber |
|---|---|---|---|---|
| GHL:Cu | 30 | 148 ± 11 | 855 ± 20 | 2.2 ± 1.2 |

NOTES TO TABLE 1:
GHL:Cu = glycyl-L-histidyl-L-lysine:copper(II)(2:1 Molar Complex)

EXAMPLE 16

Stimulation of Healing by Hydrophobic and Albumin Binding Derivatives of GHL-Cu

Groups of rats had wound chambers implanted as described in Example 10. After allowing for encapsulation of the chambers, the compounds to be tested were injected (0.2 ml at the dosage specified) directly through the rat skin and into the wound chambers. Controls received injections of saline. The chambers were harvested and the biochemical parameters of granulation tissue formation examined as described in Example 10.

As shown in Table 7, the modification of GHL-Cu by the addition of hydrophobic moieties stimulates the healing parameters in rats.

TABLE 7

EFFECT OF HYDROPHOBIC DERIVATIVES OF GHL-Cu ON WOUND HEALING

| COMPOUND | DOSE mg/injection | WET WEIGHT mg | PROTEIN mg/chamber | COLLAGEN μg HP/chamber | ANGIOGENESIS Units AP/chamber |
|---|---|---|---|---|---|
| A: | | | | | |
| SALINE | — | 85 ± 30 | 47 ± 20 | 335 ± 132 | 5.3 ± 3.6 |
| GHLW:Cu | 3.1 | 94 ± 14 | 39 ± 8 | 1508 ± 128 | 7.7 ± 1.6 |
| GHL-Octyl Amide:Cu | 2.6 | 101 ± 8 | 47 ± 6 | 1339 ± 265 | 6.7 ± 1.3 |
| B: | | | | | |
| SALINE | — | 75 ± 11 | 49 ± 9 | 703 ± 244 | 4.5 ± 1.0 |
| GHL-Octyl Ester:Cu | 2.6 | 106 ± 8 | 66 ± 8 | 1918 ± 565 | 12.4 ± 3.6 |

NOTES TO TABLE 7:
GHLW:Cu = glycyl-L-histidyl-L-lysyl-L-tryptophan:copper(II)(2:1 Molar Complex)
GHL-Octyl Ester:Cu = glycyl-L-histidyl-L-lysine octyl ester:copper(II)(2:1 Molar Complex)
GHL-Octy Amide:Cu = glycyl-L-histidyl-L-lysine octyl amide:copper(II)(2:1 Molar Complex)

EXAMPLE 17

Stimulation of Wound Healing by Sequence Variations of GHL-Cu

Groups of rats had wound chambers implanted as described in Example 10. After allowing for encapsulation of the chambers, the compounds were injected (0.2 ml at the dosage specified) directly through the rat skin and into the wound chambers. Controls received injections of saline. The chambers were harvested and the biochemical parameters of granulation tissue formation examined as described in Example 10. The results are summarized in Table 8.

TABLE 8

EFFECT OF SEQUENCE MODIFICATIONS OF GHL-Cu ON WOUND HEALING

| COMPOUND | DOSE mg/injection | WET WEIGHT mg | PROTEIN mg/chamber | COLLAGEN μg HP/chamber | ANGIOGENESIS Units AP/chamber |
|---|---|---|---|---|---|
| A: | | | | | |
| SALINE | — | 75 ± 11 | 49 ± 9 | 703 ± 244 | 4.5 ± 1.0 |
| G(3-Me)HL:Cu | 2.0 | 125 ± 15 | 75 ± 9 | 1996 ± 288 | 8.9 ± 5.5 |
| GHCap:Cu | 2.0 | 98 ± 13 | 60 ± 11 | 1699 ± 365 | 10.7 ± 3.1 |
| AHL:Cu | 2.0 | 74 ± 22 | 46 ± 14 | 1565 ± 520 | 10.2 ± 6.5 |
| HGL:Cu | 2.0 | 104 ± 13 | 58 ± 9 | 2025 ± 456 | 10.4 ± 3.9 |
| B: | | | | | |
| SALINE | — | 85 ± 30 | 47 ± 20 | 335 ± 132 | 5.3 ± 3.6 |
| LHGVFV:Cu | 3.8 | 95 ± 18 | 37 ± 9 | 1630 ± 275 | 8.0 ± 1.3 |

NOTES TO TABLE 8:
G(3-Me)HL:Cu = glycyl-L-(3-methyl)histidyl-L-lysine:copper(II)(2:1 Molar Complex)
GHCaprolactam:Cu = glycyl-L-histidyl-caprolactam:copper(II)(2:1 Molar Complex)
AHL:Cu = alanyl-L-histidyl-L-lysine:copper(II)(2:1 Molar Complex)
HGL:Cu = histidyl-glycyl-L-lysine:copper(II)(2:1 Molar Complex)
LHGVFV:Cu = lysyl-L-histidyl-glycyl-L-valyl-L-phenylalanyl-L-valine:copper(II)(2:1 Molar Complex)

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

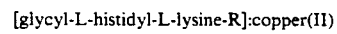

I claim:

1. A method for accelerating wound healing in a warm-blooded animal by systemically administering to the animal a therapeutically effective amount of a composition comprising a copper(II):peptide complex in combination with a pharmaceutically acceptable carrier or diluent, said complex having the general formula:

[glycyl-L-histidyl-L-lysine-R]:copper(II)

wherein R is L-tryptophan, (glycyl)$_y$-L-tryptophan, where $y=1-4$, or $(X)_n$-L-tryptophan, where X is a —$CH_2$— or —CH(OH)— moiety and $n=4-20$.